United States Patent [19]

Siegel et al.

[11] Patent Number: 5,541,115
[45] Date of Patent: Jul. 30, 1996

[54] METHOD AND DEVICE EMPLOYING COVALENTLY IMMOBILIZED COLORED DYES

[75] Inventors: Neal A. Siegel, Deerfield; Gradimir G. Georgevich, Mundelein, both of Ill.

[73] Assignee: Abbott Laboratories, Abbott Park, Ill.

[21] Appl. No.: 710,237

[22] Filed: Jun. 3, 1991

Related U.S. Application Data

[63] Continuation of Ser. No. 204,443, Jun. 9, 1988, abandoned.
[51] Int. Cl.$^6$ .................................................. G01N 33/52
[52] U.S. Cl. .......................................... 436/135; 436/169
[58] Field of Search ..................... 422/56, 55; 436/135, 436/169, 903, 904; 435/14, 28, 805

[56] References Cited

U.S. PATENT DOCUMENTS

| | | |
|---|---|---|
| 3,443,939 | 5/1969 | Bloom et al. . |
| 3,853,466 | 12/1974 | Rittersdorg et al. . |
| 3,876,504 | 4/1975 | Koffler ..................................... 435/805 |
| 3,904,373 | 9/1975 | Harper ..................................... 436/169 |
| 3,992,158 | 11/1976 | Przybylowicz et al. .................. 422/57 |
| 4,038,031 | 7/1977 | Lam . |
| 4,069,016 | 1/1978 | Wu . |
| 4,139,346 | 2/1979 | Rabbani .................................... 422/56 |
| 4,168,146 | 9/1979 | Grubb et al. ............................. 436/810 |
| 4,190,419 | 2/1980 | Bauer . |
| 4,299,916 | 11/1981 | Litman et al. . |
| 4,361,648 | 11/1982 | Shuenn-tzong . |
| 4,391,904 | 7/1983 | Litman et al. . |
| 4,435,504 | 3/1984 | Zuk et al. . |
| 4,439,527 | 3/1984 | Pakebusch et al. ...................... 436/135 |
| 4,446,232 | 5/1984 | Liotta ........................................ 422/56 |
| 4,578,245 | 3/1986 | Arai et al. ................................. 422/56 |
| 4,584,905 | 10/1985 | Wu . |
| 4,594,327 | 6/1986 | Zuk . |
| 4,671,937 | 6/1987 | Katsuyama et al. ..................... 436/904 |
| 4,672,029 | 6/1987 | Washburn et al. . |
| 4,806,311 | 2/1989 | Greenquist ................................ 422/56 |
| 4,822,746 | 3/1989 | Walt .......................................... 422/55 |
| 4,870,005 | 9/1989 | Akiyoshi et al. ......................... 422/56 |

FOREIGN PATENT DOCUMENTS

| | | |
|---|---|---|
| 0119861A1 | 9/1984 | European Pat. Off. . |
| 2095401 | 9/1982 | United Kingdom .................. 436/135 |

OTHER PUBLICATIONS

Izumi, et al., "Anti–bilirubin Monoclonal Antibody, II. Enzyme–linked Immunosorbent Assay for Bilirubin Fractions by Combination of Two Monoclonal Antibodies," Biochimica Et Biophysica Acta, 967 (1988) 261–266.

Nilsson, et al., "Immobilization of Enzymes and Affinity Ligands to Various Hydroxyl Group Carrying Supports Using Highly Reactive Sulfonyl Chlorides," Biochemical And Biophysical Research Communications, 102:1, Sep. 16, 1981, pp. 449–457.

Nilsson, et al., "[2] Immobilization of Ligands with Organic Sulfonyl Chlorides," Methods In Enzymology, vol. 104 (1984) 56–69.

Tijssen, "Practice and Theory of Enzyme Immunoassays," Laboratory Techniques In Biochemistry And Molecular Biology, vol. 15 (1985) 109–110.

*Primary Examiner*—Timothy M. McMahon

[57] ABSTRACT

A test method and device employ a matrix to which is covalently bonded a second component of a two component dye system. Color is formed when the first component, which may be the analyte or another dye component, covalently couples to the second component. The color formed is covalently immobilized to the matrix. A preferred second component, 5-amino-2-naphthalene sulfonic acid, is covalently bonded via the amino group and forms a colored covalent adduct with oxidized 4-aminoantipyrine. Another preferred second component is diazotized para-aminoaniline, which is covalently bonded via the amino group and forms a colored covalent adduct directly with bilirubin.

20 Claims, 1 Drawing Sheet

METHOD AND DEVICE EMPLOYING COVALENTLY IMMOBILIZED COLORED DYES

This application is a Continuation of application Ser. No. 07/204,443, filed Jun. 9, 1988 now abandoned.

BACKGROUND OF THE INVENTION

The present invention relates to methods and devices employing a colored dye compound covalently bound to a supporting matrix. More particularly, the colored dye compound is formed by the coupling of a first and second component of a two component dye system, the second component of which is covalently immobilized on the matrix. Addition of the first dye component forms a colored covalent adduct covalently immobilized to the matrix. The methods of making, the methods of using and the devices themselves have particular utility in test strips used in diagnostic medicine wherein the colored dye compounds are permanently affixed to the matrix and do not run or leach.

A number of methods binding a dye to a matrix are known in the art. The textile industry binds dye to textiles using mordants which, acting alone or in conjunction with a dye, become absorbed or absorbed or otherwise intercalate and become stuck on the surface or on the fibers of the textile. Because the mordants and dyes are not covalently bound to the textile, they tend to leach out with washing causing fading and discoloration.

Other methods for immobilizing dye compounds include providing a dye molecule with a higher alkyl hydrophobic side chain which inserts itself into a hydrophobic substrate or support and is immobilized by hydrophilic/hydrophobic interactions. See, for example, Bloom, et al., U.S. Pat. No. 3,443,939.

Nevertheless, colored dye compounds used in analytical test devices have been bound only unsatisfactorily to date. Typically, a colored compound is immobilized on the basis of its insolubility relative to the assay solution, which causes it to precipitate onto the matrix without covalent bonding. In other systems, generated color is absorbed, imbibed, impregnated, or coated onto the supporting matrix. Patents exemplifying this approach include U.S. Pat. Nos. 4,069,016, 4,548,905, 4,038,031. Finally, limited success at immobilizing color has been achieved by generating localized, precipitated color only at the surface of the solid phase through a signal generating enzyme system immobilized to the support. See, for example, U.S. Pat. No. 4,435,504.

It is an object of the present invention to overcome the disadvantages of the prior art and to provide methods and apparatus in which the colored indicating compound is covalently immobilized to the support and cannot leach or be washed therefrom.

SUMMARY OF THE INVENTION

In one aspect, the present invention relates to a method of preparing a solid phase matrix capable of covalently immobilizing a colored dye compound, the dye compound being formed from first and second components. The method comprises the steps of a) activating reactive groups on at least one of the matrix and the second dye component; b) covalently binding the second dye component to the matrix via the activated reactive groups, thereby to form matrix-bound second dye component; and c) contacting said matrix-bound second dye component with first dye component to form a colored covalent adduct which remains covalently immobilized on the matrix. The second dye component may be any compound which can be covalently immobilized to the support and which is capable of covalently binding with a first dye component to form a colored product.

In another aspect of the invention, an assay device for qualitatively or quantitatively determining an analyte in a fluid test sample comprises an improved solid phase having a second component of a dye system covalently bound thereto, the second component being adapted to covalently couple the analyte or first dye component proportional to the amount of analyte to form a colored dye compound covalently immobilized to the solid phase in proportion to the amount of analyte. In such an assay, the analyte must be capable of forming a colored compound when bound to the second component. Alternatively, a first dye component which is generated or rendered bindable in an amount proportional to the amount of analyte present can be coupled by the second component to form a colored covalent adduct proportional to the analyte.

In yet another aspect, the invention comprises a method of assaying for an analyte in a test sample, the method comprising contacting a solid phase matrix having covalently bound thereto a second component of a two component dye system with a liquid phase including a first component of the dye system, the amount of said first component being equal to or proportional to the amount of analyte present in the test sample, said first and second components binding covalently to form an immobilized colored dye compound; and b) determining the amount of colored dye compound covalently bound to the support as a measure of the analyte in the sample. As in the assay device, the first dye component which binds to the second dye component covalently bound to the support may be either the analyte itself or a first dye component rendered bindable to the support in proportion to the amount of analyte present. The analyte may be a specific analyte of interest, such as glucose, or it may be a marker indicative of an analyte concentration, such as peroxide produced by an enzyme system (e.g. horseradish peroxidase) conjugated to an analyte specific binding member.

"Colored" as used herein means distinguishable from the matrix. Preferably, the dye components are colorless chromogens or dye precursers, and become colored upon coupling together. It is possible, however, that the components initially have intrinsic color and couple to form a colorless or colored adduct that is distinguishable.

DETAILED DESCRIPTION

Figure 1:
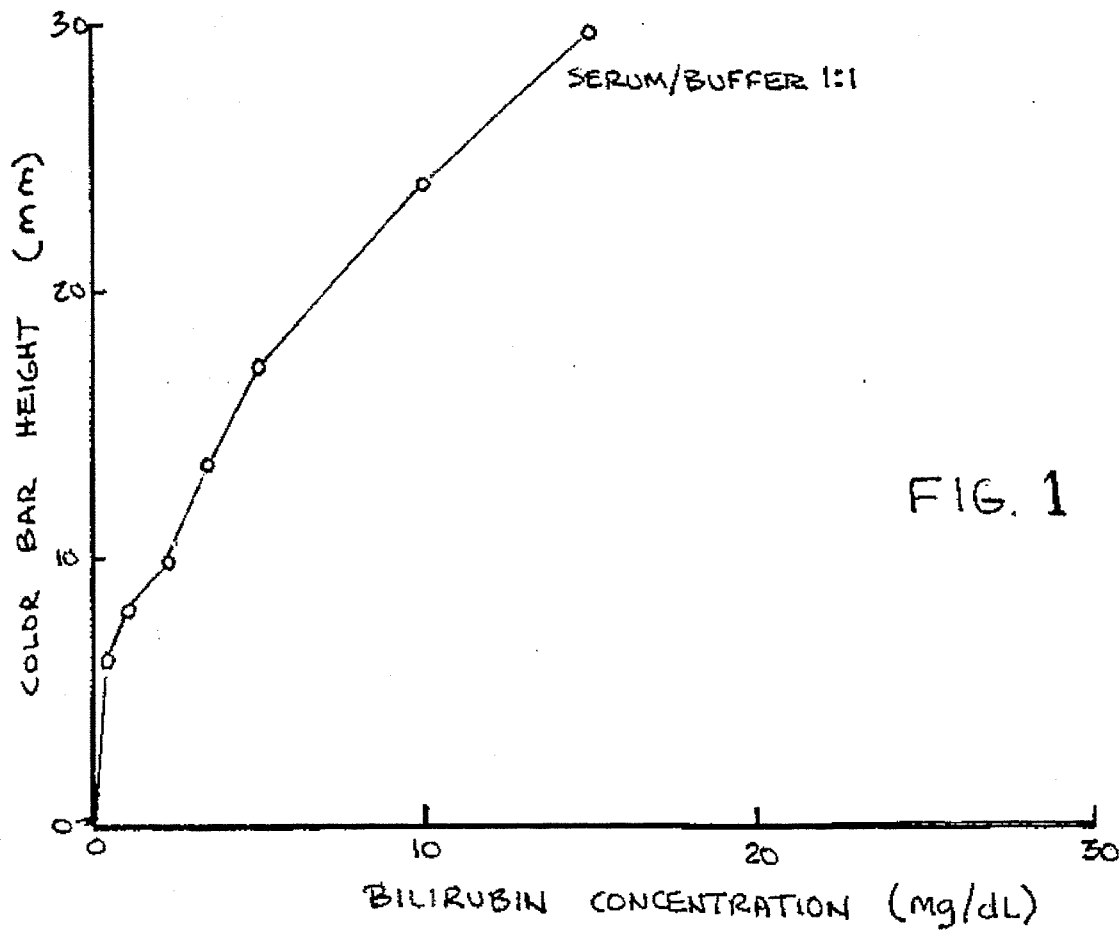
FIG. 1 is a plot of the color bar height against bilirubin concentration resulting from the use of a test strip according to the invention.

A solid phase matrix capable of covalently immobilizing a colored dye compound, the dye compound being formed from first and second components, is prepared according to the invention by: a) activating reactive groups on at least one of the matrix and the second dye component; and b) covalently binding the second dye component to the matrix via the activated reactive groups, thereby to form matrix-bound second dye component. The matrix-bound second dye component is then able to couple with first dye component to form a colored covalent adduct which remains covalently immobilized on the matrix.

Typically, reactive groups on the matrix or the second dye component comprise amino groups or preferably, hydroxyl groups. The hydroxyl groups are activated by reaction with organic sulfonyl chlorides of the formula: $R-SO_2-Cl$ to produce the corresponding sulfonate ester in the manner taught by Nilsson et al. *Biochem and Biophys Res Comm*, 102, 449–451 (1981). R in this case may be methyl, ethyl, phenyl or toluyl moieties, although moieties substituted with electron withdrawing halo groups are more preferred. Especially preferred are trifluoromethane- sulfonyl chloride; 2,2, 2-trifluoroethanesulfonyl chloride (tresyl chloride), and p-nitrobenzenesulfonyl chloride.

Alternatively, reactive hydroxyl groups may be activated by reaction with periodate as taught by Tijssen, *Laboratory Techniques in Biochemistry and Molecular Biology*, Volume 15, "Practice and Theory of Enzyme Immunoassays", page 109, Elsevier Publishers, N.Y. (1985). Although periodate activation is preferred, other methods of activating or derivatizing the matrix, including the use of spacers or linkers, are known to those of skill in the art and are not repeated here.

Matrices are insoluble in test samples and include cellulose, agarose, cross-linked dextrans, paper, diol-silica, and glycerylpropyl coated glass. Diol-silica is available from E. Merck & Co., West Germany as LiChrosorb Diol, and glass treated in this manner is commercially available from Pierce Chemical Co., Rockford, Ill., as Glycophase glass. Paper is a preferred matrix. In addition, the solid phase matrix may or may not be carried on a carrier or support. Since the matrix and support can be one and the same (e,g. paper), "support" as used herein is intended to include a matrix and is interchangeable therewith.

Once the support is activated, the second dye component is covalently bound thereto. The second dye component may be any compound which can be covalently immobilized to the support and which is capable of covalently coupling with analyte or a first dye component to form a colored product. For covalent immobilization of the second dye component to organic sulfonyl chloride activated supports, the dye component should contain nucleophilic groups, for example, sulfhydryl or amino groups. For covalent immobilization to periodate activated supports, the dye component must contain an amino group. These reactions proceed according to well known methods.

Preferred second dye components include para-unsubstituted phenolic compounds, para-unsubstituted aromatic amine compounds and para-halogenated phenolic or aromatic amine compounds. In a first embodiment the most preferred second dye component is 5-amino-2-naphthalene sulfonic acid which couples with and forms a covalent adduct with oxidized 4-aminoantipyrine or its analogs. The aminoantipyrine (or analogs) are oxidized through the conventional enzymatic cascade using an oxidase enzyme coupled with a peroxidase enzyme in a manner well known in the art.

A second embodiment utilizes a diazonium salt as the preferred second dye component which directly captures the analyte bilirubin to form a colored dye compound covalently bound to the matrix. A preferred diazonium salt is (diazotized p-aminoaniline bound to a periodate activated support.)

In another aspect of the invention, an assay device for qualitatively or quantitatively determining an analyte in a test sample comprises an improved solid phase having a second component of a dye system covalently bound thereto, the second component being adapted to covalently couple the analyte or first dye component proportional to the amount of analyte to form a colored dye compound covalently immobilized to the solid phase in proportion to the amount of analyte. In such an assay, the second dye component may couple with either the analyte itself to form a colored compound or with a first dye component which is generated or rendered bindable in an amount proportional to the amount of analyte present.

Using the preferred solid phase matrices previously described, assay devices may be prepared for detecting and/or quantifying specific analytes in various test samples. Generally, test samples will be aqueous fluids such as whole blood, serum, plasma, saliva, cerebrospinal fluid, urine, amniotic fluid and the like removed from a subject, or laboratory assay solutions. Embodiments of the assay devices include both chromatographic strips and dipstick or pad-type assays.

In the chromatographic strip embodiment, the analyte is quantitated as a function of the length of the color bar formed on the strip. More specifically, the analyte or first dye component present in the liquid phase is advanced by the solvent front over or through the matrix to which the second dye component has been covalently immobilized. As the liquid phase advances, the analyte or first dye component, to the extent present in the test sample, covalently couples with the second dye component immobilized on the support. When the analyte or first dye component is depleted, no further coupling or color formation takes place. Because the solvent front advances with time, the length of the color bar is related to the amount of analyte present. Color formed is thus permanently immobilized on the support and will not leech or wash off. Graduations marked along a border of the strip can be used to correlate length to analyte concentration.

In dipstick or pad-type analytical devices, the liquid phase is merely contacted with the solid phase and does not advance over it. Accordingly, the amount of analyte present is determined as a function of the amount of color formed on the solid phase. Intensity, fluorescence and hue are some examples of methods known in the art for determining the amount of color formed.

In some cases, e.g., bilirubin, contacting the solid phase, with the liquid phase containing the test sample will form color directly. In other cases, the liquid phase also contains a reagent means for generating a first dye component or rendering it covalently coupleable with the second dye component, the amount of first dye component generated or rendered coupleable being proportional to the amount of analyte. An example of such a reagent means is an oxidase-peroxidase enzyme system which can be used to oxidize a first dye component such as 4-aminoantipyrine (or analogs) to render it bindable with the second dye component (e.g. 5 amino-2-naphthalene sulfonic acid).

As previously mentioned, the analyte itself may be the first dye component or it may be a compound of biological interest such as glucose, cholesterol or a hormone. Alternatively, the analyte may be merely a marker which in turn is generated or rendered reactive in proportion to the actual analyte of interest. Such a case occurs when peroxide (analyte marker) is used with peroxidase to form a colored compound, the peroxidase being conjugated to an antibody, and the antibody being present in proportion to a particular antigen (actual analyte of interest). Accordingly, it is within the scope of the present invention to employ the assay devices and methods in immunoassays wherein an antibody or antigen labeled with an enzyme marker is used indirectly to render the first dye component bindable in proportion to the amount of analyte present in the sample. More specifically, an antibody conjugated to HRPO can detect an antigen in a sandwich or competitive immunoassay, and the HRPO, along with peroxide, can oxidize a first dye component to render it bindable in proportion to the amount of antigen. Such a first dye component is 4-aminoantipyrine. The first dye component (rendered bindable) can then couple with the second dye component covalently immobilized on the support to form a colored product proportional to the amount of antigen present in-the sample.

A method of use of the assay devices includes contacting the solid phase having covalently bound thereto the second dye component with a liquid phase including a first component of the dye system, the first component being present in an amount equal to or proportional to the amount of analyte in the test sample. The analyte may be synonymous with the first dye component in the liquid phase. Subsequent to this contacting, colored compound is formed on the solid phase by the covalent coupling of the first dye component with the immobilized second dye component. Thereafter, the amount of analyte is determined as a function of the amount of colored compound.

The following examples are given by way of illustration only and are not intended to limit the invention in spirit or scope, since based upon this disclosure many modifications will become obvious to those of ordinary skill in the art.

EXAMPLE 1

(Support Activation)

A. Activation of Paper with 2,2,2-Trifluoroethanesulfonyl Chloride (Tresyl Chloride)

In a typical procedure 10 g (wet) of Whatman brand #0541 grade paper is washed successively with 100 ml of each of the following: 30:70 and 70:30 of acetone:water (v/v), twice with acetone and three times with dry acetone (dried with 4A molecular sieve overnight using 25 g per liter of acetone). The paper is then transferred to a dried beaker containing 3 ml of dry acetone and 150 μl of dry pyridine (dried with molecular sieves). During agitation, 100 μl of tresyl chloride (Fluka AG, Buchs, Switzerland) is added dropwise. After 10 minutes at room temperature, the paper is washed twice with 100 ml of each of the following: acetone, 30:70, 50:50, and 70:30 of 5 mM HCl:acetone (v/v); and 1 mM HCl. The activated paper is stored at 4° C. until used.

The amount of introduced tresyl groups was determined by elemental analysis for sulfur on a sample of freeze dried paper prepared as above. The analysis indicated 150 umol of tresyl groups per gram of dry paper.

B. Activation of A Hydroxyl Bearing Support (Paper) With Periodate

To a solution of 10 g of sodium periodate in 200 ml of distilled water at room temperature was added 10 g of Schleicher and Schuell grade 410 filter paper. The paper and solution were agitated on a rotary shaker for 3 hours. Thereafter, the periodate solution was poured off and 200 ml of distilled water was added. After 15 minutes. the water was poured off and another 200 ml of fresh distilled water was added. This last step was repeated two additional times to produce an activated paper ready for coupling.

EXAMPLE 2

A. Coupling 5-Amino-2-Naphthalene Sulfonic Acid to Paper

To 100 ml of 0.1M sodium phosphate buffer pH 7.4 was dissolved 0.5 g of 5-amino-2-naphthalene sulfonic acid (ANS) and 0.75 g of recrystalized sodium cyanoborohydride. This solution was then added to a vessel containing the activated paper of Example 2. The combined solution and paper were agitated overnight at room temperature on a rotary shaker. Optionally, the time could be increased or decreased to effect more or less binding respectively. After incubation, the ANS solution was poured off the dye coupled paper (ANS paper) and the ANS paper was rinsed once with 200 ml of distilled water. The ANS paper was then washed with 200 ml of fresh distilled water every 30 minutes until the ANS concentration fell below 5 mg/ml. The, sheets were allowed to air dry prior to use.

B. Activation and Coupling of 5-Amino-2-Naphthalene Sulfonic Acid to Glass Fiber Filters Activation A glass fiber filter (Schleicher and Schuell #29) was washed overnight in 6M nitric acid. Thereafter, it was rinsed in deionized water and air dried. The glass fiber filter was then placed in a 10% solution of 3-glycidoxypropyltrimethoxysilane buffered with 10 mM citrate pH 5.0 and incubated at 50° C. for 30 minutes. The resulting glycophase glass filter was then washed in acetone, acetone/water mixtures and finally water. Thereafter, the filter was incubated overnight in 1% $NaI_{o4}$ to generate aldehydes. The filter was then washed with water until the periodate was essentially removed. The filter was then incubated overnight in a solution comprising 1% (v/v) solution of 5-amino-2-naphthalene sulfonic acid, 100 mM $NaCNBH_3$, and 100 mM sodium phosphate pH 7.4. After the incubation, the product was washed exhaustively in water to remove unbound material, and air dried for further storage.

EXAMPLE 3

Coupling p-amino aniline to a support and diazotizing

Cellulose filter papers (Whatman #1 and S&S 410) were oxidized in 1% w/v $NaIO_4$ (periodate) overnight at room temperature with agitation. Papers were then washed in water to remove excess periodate. Papers were then incubated for 2 and ½ days at room temperature in 100 mM p-aminoaniline, 20 mM sodium phosphate at ph 7.4, and 100 mMNaCNBH$_3$ to derivatize the papers. About 10 volumes of solution were used per paper weight. The papers were then washed several times first with PBS and then with water. Available amines were diazotized by incubating the papers for 10 minutes on ice in 6% (w/v aqueous solution) hexafluorophosphoric acid and 50 mM sodium nitrite. The diazotized papers were washed in water, air dried and stored in dark, cold and dry place.

EXAMPLE 4

A. Preparation of Standard Solutions 1. 0.5 M Phosphate Buffer pH 7.4

A 0.5 M $Na_2HPO_4$ solution is titrated with a 0.5 M $NaH_2PO_4$ solution until a pH 7.4 is achieved.

2. Stock Glucose Solutions

To 100 ml of 0.1M phosphate buffer pH 7.4 (100 ml. of 0.5 M phosphate buffer pH 7.4 diluted to 500 ml with distilled water) was added 1,000 mg glucose to make a 1000 mg/dL glucose stock solution. This solution was repeatedly diluted by a factor of 2 to yield glucose solutions of 500 mg/dL, 250 mg/dL, 125 mg/dL and 63 mg/dL.

3. Enyzme Solutions a. Glucose Oxidase Solution

To 10 ml of 0.1M (1.95 g/100 ml of deionized water) MES (2[N-morpholino]ethane sulfonic acid) adjusted to pH 5.6 with 0.1 N NaOH was added 1,000 units of glucose oxidase, 30 mg of 4-aminoantipyrine, and 5 units mutarotase. The mixture was gently swirled to effect dissolution.

b. Peroxidase Solution

To 10 ml of 0.1M MES, prepared from 1.95 g of 2[N-morpholino]ethane sulfonic acid dissolved in 100 ml of deionized water, was added 300 units of horseradish peroxidase.

EXAMPLE 5

Preparation of Diagnostic Test Strips for Glucose Using ANS Paper

A. Method 1

To a 20 µl drop of the 1,000 mg/dL glucose standard solution, was added 1 µl each of the glucose oxidase solution and the peroxidase solution. The solutions were mixed for 5 seconds. Into the solution was dipped the bottom margin of a narrow strip of 5-ANS dye coupled paper (Example 2A) which had been cut small enough so that the solution would wick its entire length. This procedure was repeated for each standard glucose solution.

B. Method 2

To one end a strip of 5-ANS dye coupled paper from Example 2A, which had been cut small enough so that 20 ml would entirely wet it, was pipetted about 1 µl of glucose oxidase solution. Immediately adjacent thereto was pipetted about 1 µl of peroxidase solution. The test strip was air dried and its bottom margin was dipped into 20 µl of the 1,000 mg/dL standard glucose solution. When the liquid phase reached the top the test was considered complete. This procedure was repeated for each standard glucose solution.

C. Reading Results

A color bar developed on the wetted strip due to the coupling of the oxidized 4-aminoantipyrine with the 5-ANS covalently bonded to the paper. The height of the color bar was found to be proportional to the concentration of glucose in the stock glucose test solutions as shown in Table 1.

TABLE 1

| COLOR BAR HEIGHT vs GLUCOSE CONCENTRATION | | | |
| --- | --- | --- | --- |
| Glucose(mg/dL) | Color Height(cm) | Std Dev | Number |
| 63 | 1.24 | .34 | 14 |
| 125 | 1.76 | .33 | 12 |
| 250 | 2.09 | .34 | 10 |

*r = 0.94

EXAMPLE 6

Preparation of a Diagnostic Test Strip for Bilirubin

A. A sheet (47 mm wide) of diazotized paper from Example #3 was attached to a plastic backing for support and evaporation control by pressing it onto an adhesive microtiter plate cover. A 1.5 mm inert paper wick (Schleicher & Schuell 410) was attached to an edge of the diazotized paper and the assembly was covered with another microtiter plate cover to sandwich the paper. Multiple test strips of about 1.5 mm were cut from the sandwich assembly, each having a diazotized zone and a wick portion.

B. Bilirubin solutions were prepared by dissolving 60 mg bilirubin (Sigma Chemicals, St. Louis) in 2 ml DMSO and 4 ml 0.1M $Na_2CO_3$ to make a stock solution. Sufficient quantities of the bilirubin stock solution were added to 200 mM carbonate, pH 10.5, 150mM diphylline and 0.2% TX-100 to make working dilutions of 0, 1, 3.5, 7.5, 10, 20 and 30 mg bilirubin/dl.

C. Working dilutions of bilirubin were mixed with equal volumes of normal human plasma to prepare test samples. Twenty microliters of each of the test samples was added to a microtiter plate well and the wick end of a test strip was contacted with each sample at room temperature (about 20° C.). After 5 minutes the front had reached the top of the test element and the results were read. The height of the color bar generated on the test element was measured and plotted against bilirubin concentration to give FIG. 1.

EXAMPLE 7

Preparation of a Diagnostic Test Strip for Cholesterol using ANS Paper

A. ANS paper from Example 2A, which had been cut small enough so that 10 µl would entirely wet it, was impregnated with The following solutions: To a first (indicator) region of the strip was pipetted about 1 µl each of: a) a 1 mg/ml HRPO solution and 2 mg/ml 4-aminoantipyrine solution; To a second (reaction) region adjacent the indicator region was pipetted about 1 µl of each of: a 100 mg/dl cholesterol oxidase solution and a 10 mg/dl cholesterol esterase solution. A third region was impregnated with about 1 µl of 5% Triton X-100 and the remainder of the strip was left blank. The strips were frozen and lyophilized prior to use.

B. Standard cholesterol solutions were obtained from Sigma Chemical Co., St. Louis, in a calibrator kit having 100, 200 and 400 mg/dl concentrations. A 300 mg/dl concentration was prepared by dilution of the 400 mg/dl standard.

Figure 2:
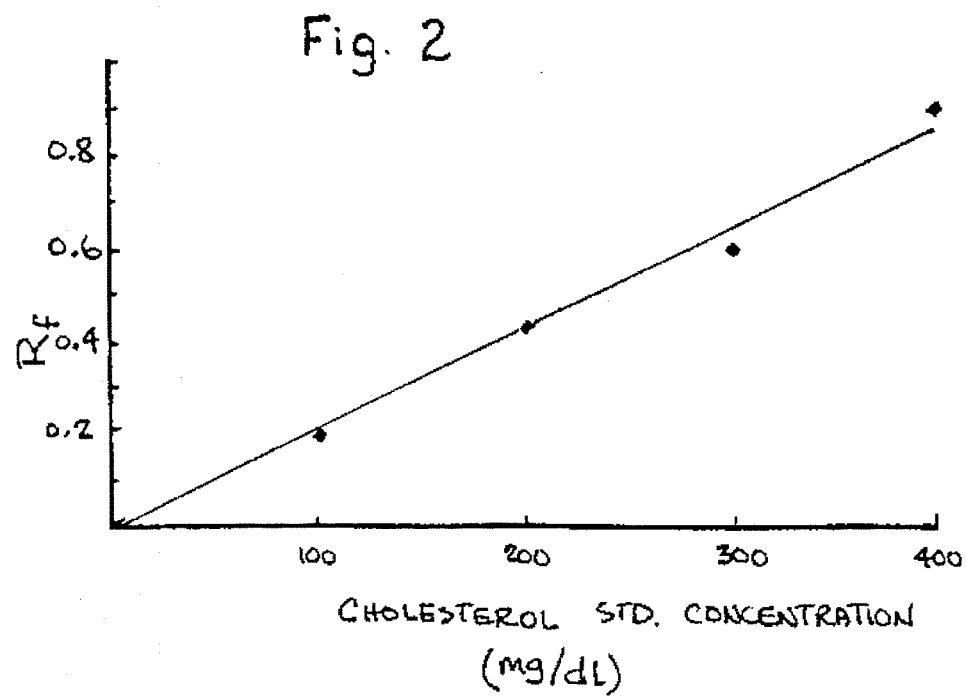
FIG. 2 is a plot of the $R_f$ values of the color bar length against cholesterol concentration.

C. About 10 µl of each of the standard cholesterol solutions was placed in microtiter plate wells. The blank region of the test strips were dipped into the wells and the solutions wicked up the strips. An $R_f$ index was calculated as the length of the color bar (measured from the border between the first and second regions to its end) divided by the length of the solvent front from the border. The length of the color bar was found to be proportional to the concentration of cholesterol in the test solutions as shown in FIG. 2.

What is claimed is:

1. A method of qualitatively or quantitatively determining the presence or amount of an analyte in a test sample, comprising the steps of:

a) contacting a solid phase matrix to a liquid phase,
      said solid phase matrix having covalently bound thereto a second component of a two component dye system, and
      said liquid phase containing a first component of said dye system, the amount of said first component being equal to or proportional to the amount of analyte present in the test sample, whereby said second component further covalently binds said first component thereby forming a permanently colored covalent adduct that ramains covalently bound to said solid phase matrix; and b) determining the presence or amount of said colored covalent adduct on said solid phase matrix as a measure of the presence or amount of the analyte in the test sample.

2. The method according to claim 1 wherein the analyte is a peroxide.

3. The method according to claim 1 wherein the first dye component is the analyte.

4. The method according to claim 1 wherein said first and second components are initially colored and covalently bind to form a distinguishable colored compound.

5. The method according to claim 1 wherein said first and second components are initially colorless and covalently bind to form a colored compound.

6. The method according to claim 1 wherein said first component is generated by a reagent means in an amount proportional to the amount of analyte in the test sample.

7. The method according to claim 1 wherein a reagent means renders said first component covalently coupleable to said second component in an amount proportional to the amount of analyte in the test sample.

8. The method according to claim 7 wherein said reagent means is an oxidase-peroxidase enzyme system.

9. The method according to claim 1 wherein said solid phase matrix is a chromatographic strip through which said liquid phase advances from an origin to a terminus, and wherein said colored dye compound is produced on said strip in the form of a color bar, the length of said color bar being proportional to the amount of analyte present in said test sample.

10. The method according to claim 1 wherein said second component is covalently bound to said solid phase matrix by activating reactive groups on at least one of said solid phase matrix and said second component and covalently binding said second component to said solid phase matrix via said activated reactive groups.

11. The method according to claim 1, wherein said matrix is a chromatographic strip and the presence or amount of the analyte in the test sample is proportional to the length of said colored covalent adduct immobilized along the length of said strip.

12. The method according to claim 1, wherein the amount of the analyte in the test sample is proportional to the intensity of said colored covalent adduct immobilized on said matrix.

13. A method of qualitatively or quantitatively determining the presence or amount of an analyte in a test sample, comprising the steps of:

a) contacting a solid phase matrix to a liquid phase, said solid phase matrix having covalently bound thereto a second component of a two component dye system, said second component selected from the group consisting of para-unsubstituted phenolic components, para-unsubstituted aromatic amine compounds and para-halogenated phenolic or aromatic amine compounds, and said liquid phase containing a first component of said dye system, the amount of said first component being equal to or proportional to the amount of analyte present in the test sample, whereby said second component further covalently binds said first component thereby forming a permanently colored covalent adduct that remains covalently bound to said solid phase matrix; and b) determining the presence or amount of said colored covalent adduct on said solid phase matrix as a measure of the presence or amount of the analyte in the test sample.

14. The method according to claim 13, wherein said first component is 4-aminoantipyrine.

15. The method according to claim 13, wherein said second component is 5-amino-2-naphthalene sulfonic acid.

16. The method according to claim 13, wherein said matrix is a chromatographic strip and the presence or amount of the analyte in the test sample is proportional to the length of said colored covalent adduct immobilized along the length of said strip.

17. The method according to claim 13, wherein the amount of the analyte in the test sample is proportional to the intensity of said colored covalent adduct immobilized on said matrix.

18. A method of qualitatively or quantitatively determining the presence or amount of an analyte in a test sample, comprising the steps of:

a) contacting a chromatographic strip to a liquid phase, said strip having covalently bound thereto a second component of a two component dye system, and said liquid phase containing the analyte which is a first component of said dye system, and a reagent means which renders the analyte reactive with said second component, whereby said second component covalently binds said reactive analyte thereby forming a permanently colored covalent adduct that remains covalently bound to said strip; and b) determining the presence or amount of said colored covalent adduct on said strip as a measure of the presence or amount of the analyte in the test sample.

19. The method according to claim 18, wherein the presence or amount of the analyte in the test sample is proportional to the length of said colored covalent adduct immobilized along the length of said strip.

20. The method according to claim 18, wherein the amount of the analyte in the test sample is proportional to the intensity of said colored covalent adduct immobilized on said matrix.

* * * * *

UNITED STATES PATENT AND TRADEMARK OFFICE
CERTIFICATE OF CORRECTION

PATENT NO. : 5,541,115  Page 1 of 2
DATED : July 30, 1996
INVENTOR(S) : N. A. Siegel, et. Al.

It is certified that error appears in the above-indentified patent and that said Letters Patent is hereby corrected as shown below:

Column 5, line 9, change "in-the" to --in the--.

Column 5, line 34, change "2, 2, 2" to --2.2.2--.

Column 5, line 38, change "#0541" to --#541--.

Column 6, line 18, change "5 mg/ml" to --5 µg/ml--.

Column 6, line 18, change "The," to --The--.

Column 6, line 32, change "$NaI_{04}$" to --$NaIO_4$--.

Column 6, line 51, change "$mMNaCNBH_3$" to --mM $NaCNBH_3$--.

Column 7, line 1, change "mi." to --ml--.

Column 7, line 36, change "20 ml" to --20 µl--.

Column 8, line 30, change "The" to --the--.

UNITED STATES PATENT AND TRADEMARK OFFICE
CERTIFICATE OF CORRECTION

PATENT NO. : 5,541,115
DATED : N. A. Siegel, et. Al.
INVENTOR(S) : July 30, 1996

It is certified that error appears in the above-indentified patent and that said Letters Patent is hereby corrected as shown below:

Column 8, line 43, change "100,200" to --100, 200--.

Signed and Sealed this

Twenty-fourth Day of December, 1996

*Attest:*

BRUCE LEHMAN

*Attesting Officer*  *Commissioner of Patents and Trademarks*